US006415693B1

(12) United States Patent
Simon et al.

(10) Patent No.: US 6,415,693 B1
(45) Date of Patent: Jul. 9, 2002

(54) SLEEVE-SHAPED DEVICE TO RETAIN SCREWS WHILE THESE ARE TURNED INTO AN OBJECT SUCH AS A BONE BY MEANS OF A SCREW DRIVER

(75) Inventors: Bernd Simon; Ole Prien, both of Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/921,220

(22) Filed: Aug. 2, 2001

(30) Foreign Application Priority Data

Aug. 12, 2000 (DE) ..................... 200 13 905 U

(51) Int. Cl.⁷ ............................. B25B 23/08
(52) U.S. Cl. ......................... 81/453; 81/455
(58) Field of Search ................... 81/453, 455, 452, 81/443

(56) References Cited

U.S. PATENT DOCUMENTS

| 1,628,144 | A | * | 5/1927 | Herrmann | 81/453 |
|---|---|---|---|---|---|
| 1,791,771 | A | * | 2/1931 | Velepec | 81/453 |
| 2,302,691 | A | * | 11/1942 | Green | 81/453 |
| 2,625,967 | A | * | 1/1953 | Stull | 81/453 |
| 2,684,698 | A | * | 7/1954 | Shaff | 81/453 |
| 3,102,565 | A | * | 9/1963 | Tomlin | 81/453 |
| 3,498,351 | A | | 3/1970 | Edwards et al. | |
| 4,363,250 | A | * | 12/1982 | Suga | 81/455 |
| 4,763,548 | A | | 8/1988 | Leibinger et al. | 81/453 |
| 4,779,494 | A | * | 10/1988 | Quach | 81/443 |
| 6,189,422 | B1 | * | 2/2001 | Stihl | 81/452 |
| 6,286,401 | B1 | * | 9/2001 | Hajianpour | 81/453 |

FOREIGN PATENT DOCUMENTS

| DE | 35 39 502 C1 | 2/1987 |
|---|---|---|
| DE | 37 14994 C1 | 6/1988 |
| DE | 44 41 965 C1 | 6/1996 |
| DE | 198 32 303 A1 | 1/2000 |

\* cited by examiner

*Primary Examiner*—Joseph J. Hail, III
*Assistant Examiner*—Hadi Shakeri
(74) *Attorney, Agent, or Firm*—Lerner, David, Littenberg, Krumholz & Mentlik, LLP

(57) ABSTRACT

A device to retain screws during insertion into an object such as a bone by use of a screw-driver. The device comprises comprising a gripping sleeve the free end of which has a radially expandable portion for receiving the screw and the other end of which has at least one radial bore for movably receiving a locking ball. A safety sleeve is slidingly disposed on an outer surface of the gripping sleeve. The safety sleeve blocks an expansion of the expandable portion when in a position which is toward the free end with respect to the gripping sleeve and releases the expandable portion when in a position which is toward the free end with respect to the gripping sleeve. A handle is axially movable and hold the first locking ball in engagement with an annular groove of the gripping sleeve. A first spring acts between an inner shoulder at the end of the handle portion facing the expandable portion and a radial shoulder of the safety sleeve. An interlocking mechanism is provided acting between the safety sleeve and the gripping sleeve, which axially secures the safety sleeve in a blocking position relative to the gripping sleeve.

23 Claims, 1 Drawing Sheet

SLEEVE-SHAPED DEVICE TO RETAIN SCREWS WHILE THESE ARE TURNED INTO AN OBJECT SUCH AS A BONE BY MEANS OF A SCREW DRIVER

BACKGROUND OF THE INVENTION

The invention relates to a sleeve-shaped device to retain screws while these are turned into an object, such as a bone, by means of a screw-driver.

Devices of such a type have been generally known as shown in U.S. Pat. Nos. 3,498,351 and 4,763,548. For example, such devices make it easier for a surgeon to screw in bone screws or similar screws under poor handling and visual conditions. The expandable portion serves for receiving the screw, particularly the screw head and, thus, enables a screw to be received at a location remote from the object. Here, the shank of the screw-driver may already be within the catch or gripping sleeve and its blade or its corresponding engaging end may already have been brought into engagement with the screw. The safety sleeve is displaceable on the catch or gripping sleeve and serves for locking the expandable portion in order that the screw be caught in the catch sleeve during the turn-in operation. For this purpose, the safety sleeve is slidingly movable between two positions on the catch sleeve. It takes its blocking positioning when in the front position, and allows an expansion of the expandable portion, when in the rear position. This allows the device to receive a screw or to be removed from the screw which was turned in.

The safety sleeve usually is biased towards the blocking position by means of a spring. However, if such a device is inserted there is a risk of the safety sleeve being pushed back against the spring, e.g. by surrounding soft parts, while the device is being inserted into the location at which a screw is intended to be turned in, which no longer guarantees the securing function of the safety sleeve.

SUMMARY OF THE INVENTION

Therefore, it is the object of this invention to provide a sleeve-shaped device to retain screws while these are turned into an object by means of a screw-driver wherein the safety sleeve maintains it blocking position regardless of external forces engaging it.

According to the invention, the safety sleeve is locked on the catch sleeve, i.e. by means of at least one ball, for example mounted on the safety sleeve. The ball engages an annular groove in the catch sleeve and is impeded by an inner portion of the second handle portion from moving outwardly. If the second handle portion is moved relative to the safety sleeve or the catch sleeve relative motion initially does not take place between the sleeves, i.e. the safety sleeve thus cannot be moved into the releasing position from the blocking position. Not until the second handle portion reaches a relative position in which the ball may escape into a recess within the second handle portion which may occur while a first spring is compressed between the handle portion and a shoulder of the safety sleeve. The first spring may move the safety sleeve again with respect to the second handle portion towards a stop into a releasing position. The second handle portion initially has moved away from the safety sleeve during its motion while the first spring is compressed.

After the locking mechanism is released the safety sleeve is allowed to follow by sliding while the first spring is released so that the expandable portion now can receive or release a screw. The shank of the screw-driver which is passed through the catch sleeve is located by means of another locking ball which engages an annular groove of the shank. Also here, a portion of the second handle portion normally prevents the locking ball from moving out. If the two components are intended to be separated from each other the second handle portion is required to move a predetermined distance relative to the catch sleeve against the force of the further spring until the aforementioned locking ball enters a further recess of the second handle portion. The distance required to be passed through here is larger than the distance which is needed for a relative motion between the second handle portion and the safety sleeve in order that this locking ball can be moved into the releasing position.

It follows from the above explanation that the safety sleeve, when in the blocking position, is prevented from axially moving to the releasing position and, thus, cannot be displaced by forces applied from the outside. Such forces, for example, will occur if the assembly is passed through a tissue until the screw which has been received is screwed in the desired location, e.g. into a bone.

According to an aspect of the invention, the first spring preferably is weaker than the second spring. According to another aspect of the invention, the second handle portion has a sleeve portion and a handling portion which are in an operative communication with each other. For example, the sleeve portion may be screwed onto an axial collar of the handling portion.

According to a further aspect of the invention, the second inner shoulder of the second handle portion and the radial recess are defined by a ring which is disposed within the second handle portion. For example, the ring may be screwed into the sleeve-shaped portion of the second handle portion. The described recesses into which the locking balls may escape preferably are formed in a ring shape in the interior of the second handle portion.

BRIEF DESCRIPTION OF THE DRAWINGS

The invention will now be explained in greater detail with reference to an embodiment shown in a drawing.

DETAILED DESCRIPTION

Figure 1:
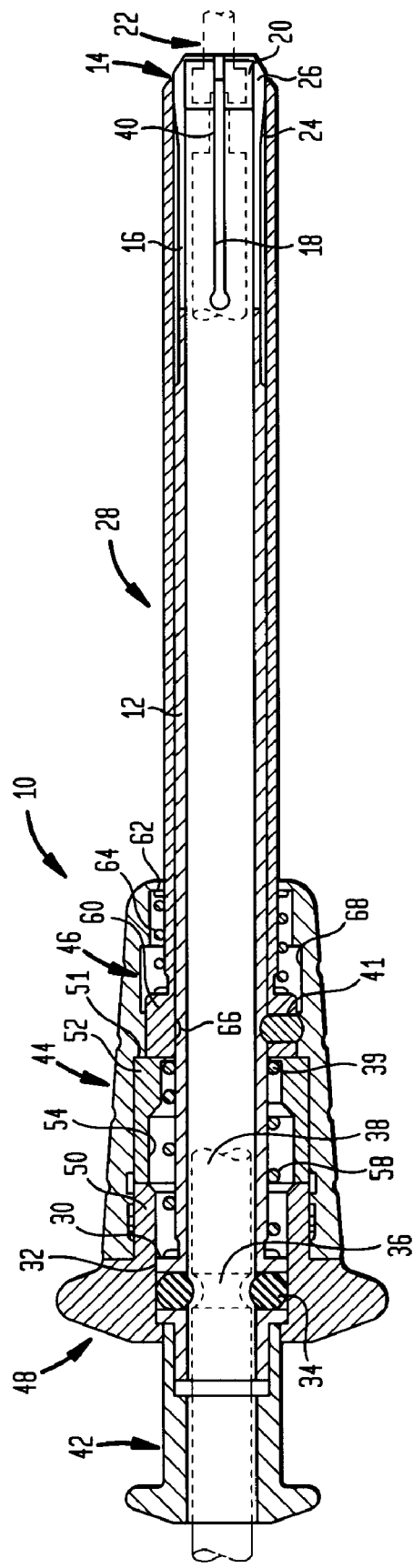
FIG. 1 shows a section through the sleeve-shaped device of the present invention with the screw-driver and screw being shown in phantom.

The preferred retaining device 10 illustrated in FIG. 1 has an inner catch sleeve 12 including an expandable portion 14 at a first end of the device shown in FIG. 1, which portion 14 consists of individual resilient segments 16 which are longitudinally separated in the circumferential direction by means of slots 18 that extend in an axially parallel relationship. At the first end or free end of the device, the segments 16 internally define a recess 20 to receive the head of screw 22 shown in phantom. A catch sleeve of this type is generally known in the, prior art. The segments 16 each have an external ramp surface 24 which extends towards the first end in a thickened portion 26.

A preferred safety sleeve 28 which is shown in its blocking position in FIG. 1, slides on the catch sleeve 12. It spreads over the thickened portions 26 of portion 14, thus preventing the segments 16 from radially expanding outwardly. Thus, a screw 22 which has been received in recess 20 is prevented from falling out or coming off.

At its opposite second end, adjacent the handle 42, the catch sleeve 12 has a radial collar 30 which holds locking balls 34 in opposed bores 32. As can be seen in the drawing the locking balls interact with an annular groove 36 of a shank 38 of a screw-driver which is shown in phantom but not in detail. The shank 38 of the screw-driver is passed through the whole catch sleeve 12 and a blade 40 or the like interacts with the head of the screw 22 in order to turn it into an object which is not shown, e.g. a bone. While in the preferred embodiment two balls 34 are used. One or more first locking balls 34 may be used.

At the second end of catch sleeve 12, a sleeve-shaped first handle portion 42 is seated with a bore which is coaxial with the bore of the catch sleeve 12. A second handle portion 44 encircles the sleeves 12 and 28 at the second end of the device and engages a portion of the first handle portion 42 facing the first end. The handle portion 44 has an external sleeve portion 46 which is conical externally and a handle portion 48 with the part of the sleeve portion 46 towards the second end being screwed onto an axial collar 50 of the handle portion 48. A ring 52 is seated in the sleeve portion 46 between the collar 50 and an inner shoulder 51 of the second handle portion 44. The ring has a radial annular recess 54 and a helical spring 58 is disposed between an inner radial shoulder 56 the ring 52 and the radial collar 30 of the catch sleeve 12.

A spring 64 is disposed between a radial collar 60 and an inner radial shoulder 62 of the sleeve portion 46. In the preferred embodiment, it also is a helical spring. The radial collar 60 receives at least one second locking ball 41 located adjacent groove 66 in sleeve 12, which ball is radially movable in an appropriate bore in collar 60 and is unable to radially escape outwardly when the parts are in the position shown in the FIGURE. The second ball acts in conjunction with outer annular groove 66 of the catch sleeve 12. The sleeve portion 46 has an inner annular groove or recess 68 into which the aforementioned second locking ball can radially escape if the annular collar 60 is within the recess 68. Upon escape, the second locking ball 41 disengages from sleeve 12. This allows sleeve 28 and collar 60, which may be integral therewith, to move towards the second end under the action of spring 64.

The description of how the device shown functions is based on the illustration in the FIGURE in which the expandable portion 14 has received the head of a screw and the safety sleeve 28 blocks the expansion of expandable portion 14. Now, a screw can be turned into an object by means of the screw-driver which has been received in the device. The mechanism interlocking the two sleeves 12, 28 against movement relative to each other makes it impossible for forces applied from the outside to push the safety sleeve 28 rearwards (towards the second end) and the expandable portion to be expanded. If the device now is to be separated from the screw 22 handle portion 48 is pulled towards first handle portion 42 while the springs 58, 64 are compressed without the safety sleeve 28 abandoning its position relative to the catch sleeve 12. This causes the ring 52 to move away from the radial collar 60, i.e. for a time until the collar 60 is in the recess 68 and the second locking ball 41 can radially escape. If this is the case the spring 64 pushes the safety sleeve 28 towards the ring 52 again until it hits against it. As a result, the safety sleeve 28 assumes its releasing position and since the expandable portion 14 is expanded the device may be removed from the head of the screw 22. Usually, the handle 44 will be retracted even farther until the balls 34 slide into the recess 54 and, thus, enable the entire assembly to be displaced on the shank 38 against a step (not shown) against which first handle portion 42 strikes in order to assume a defined position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for retaining screws during insertion into an object such as a bone by use of a screw-driver, comprising:

a catch sleeve having a free end which has a radially expandable portion for receiving the screw and another end having at least one radial bore for movably receiving a first locking ball which interacts with an annular groove in a shank of a screw-driver;

a safety sleeve slidingly disposed on the catch sleeve, which blocks an expansion of the expandable portion when in a position which is adjacent to the free end of the catch sleeve and releases the expandable portion when in a position which is retracted with respect to the catch sleeve;

a first handle portion connected to the catch sleeve;

a sleeve-shaped, second handle portion which encircles the catch sleeve and the safety sleeve and is axially movable with respect to the first handle portion and holds the first locking ball in engagement with the annular groove of the screw-driver shank;

a first spring extending between a first inner shoulder at an end of the second handle portion facing the expandable portion and a radial shoulder of the safety sleeve;

an interlocking mechanism acting between the safety sleeve and the catch sleeve, which mechanism axially secures the safety sleeve in a blocking position relative to the catch sleeve and is actuated by the second handle portion upon its movement a predetermined distance relative to the sleeves.

2. The screw retaining apparatus according to claim 1, further comprising:

a second locking ball which is movably mounted in a radial bore of a collar on the safety sleeve, said second bill interacts with an annular groove of the catch sleeve, and is held by the second handle portion in engagement with the annular groove of the catch sleeve;

a second spring located between a radial shoulder of the second handle portion and a radial shoulder of the catch sleeve;

an inner radial recess in the second handle portion, which can be entered by the second locking ball if the second handle portion is moved a predetermined first distance relative to the safety sleeve while the first and second springs are compressed, which causes the first spring to urge the safety sleeve into a releasing position; and a second inner radial recess in the second handle portion which the first locking ball enters if the second handle portion is moved a predetermined second distance relative to the safety sleeve and the first handle portion when the second spring is compressed, with the second distance being longer than the first distance.

3. The device according to claim 2, wherein the first spring is weaker than the second spring.

4. The device according to claim 1, wherein the first spring is weaker than the second spring.

5. The device according to claim 1, wherein the second handle portion has a sleeve portion and a handling portion which are in an operative communication.

6. The device according to claim 1, wherein a second inner shoulder of the second handle portion and the radial recess are defined by a ring which is disposed within the second handle portion.

7. A screw retaining device comprising:
- an inner sleeve extending along a longitudinal axis and having a first end with a gripping segment for selectively gripping and releasing a head of a screw;
- an outer sleeve extending along said axis for sliding engagement with an outer surface of said inner sleeve, said outer sleeve moveable along said axis towards and away from said first end of said inner sleeve and selectively engaging and disengaging said gripping segment causing said selective gripping and releasing of the screw head;
- a first locking element mounted on said outer sleeve for selective engagement with said inner sleeve to selectively prevent relative movement therebetween along said axis;
- a handle slidably mounted on said outer sleeve including a first inner portion for engaging said locking element when at a first position along said axis to maintain said locking element in engagement with said inner and outer sleeves and having a second inner portion for allowing movement of said locking element for releasing said engagement between said inner and outer sleeves when at a second position along said axis.

8. The screw retaining device as set forth in claim 7 further including a first spring acting between said handle and said outer sleeve.

9. The screw retaining device as set forth in claim 8 further including a second locking element mounted on said inner sleeve for selective engagement with a shank of a screw-driver mounted within said inner sleeve.

10. The screw retaining device as set forth in claim 9 further including a second spring acting between said handle and said inner sleeve.

11. The screw retaining device as set forth in claim 10 wherein said handle has a second inner portion for engaging said second locking element at a first position along said axis with respect to said inner sleeve for maintaining said second locking element in engagement with said inner sleeve and said screw shank and releasing said engagement when at a second position along said axis with respect to said inner sleeve.

12. The screw retaining system as set forth in claim 11 wherein movement of said handle along said axis in a direction away from said first end releases said first locking element before releasing said second locking element.

13. The screw retaining device as set forth in claim 8 wherein movement of said handle along said axis in a direction away from said first end of said inner sleeve causes movement of said handle from said first position to said second position releasing said locking element and causing said outer sleeve to move relative to said inner sleeve under the action of said first spring in a direction away from said first end to selectively release said gripping of said screw by said inner sleeve.

14. The screw retaining device as set forth in claim 13 further including a second locking element mounted on said inner sleeve for selective engagement with a shank of a screw-driver mounted within said inner sleeve.

15. The screw retaining device as set forth in claim 14 further including a second spring acting between said handle and said inner sleeve.

16. The screw retaining device as set forth in claim 15 wherein said handle has a second inner portion for engaging said second locking element at a first position along said axis for maintaining said second locking element in engagement with said inner sleeve and said screw shank and releasing said engagement when at a second position along said axis with respect to said inner sleeve.

17. The screw retaining system as set forth in claim 16 wherein movement of said handle along said axis in a direction away from said first end releases said first locking element before releasing said second locking element.

18. The screw retaining device of claim 7 wherein said handle portion has an inner bore and said outer sleeve has an outwardly extending collar slidably received within said inner bore of said handle portion, said first locking element mounted in said collar and engaging said inner bore of said handle portion at said first axial position and entering a recess in said handle portion at said second axial position.

19. The screw retaining device as set forth in claim 18 further including a first spring acting between said handle and said outer sleeve.

20. The screw retaining device as set forth in claim 19 wherein movement of said handle along said axis in a direction away from said first end causes relative movement of said handle and said collar from said first position to said second position releasing said locking element and causing said outer sleeve to move relative to said inner sleeve under the action of said first spring in a direction away from said first end to selectively release said gripping of said screw by said inner sleeve.

21. A screw retaining device comprising:
- an inner sleeve extending along a longitudinal axis and having a first end with a gripping segment for selectively gripping and releasing a head of a screw;
- an outer sleeve extending along said axis for sliding engagement with an outer surface of said inner sleeve, said outer sleeve moveable along said axis towards and away from said first end of said inner sleeve and selectively engaging and disengaging said gripping segment causing said selective gripping and releasing of the screw head;
- a first locking element mounted on said outer sleeve for selective engagement with said inner sleeve to selectively prevent relative movement therebetween along said axis and a second locking element mounted on said inner sleeve for selective engagement with a shank of a screw-driver mounted within said inner sleeve; and
- a handle slidably mounted on said outer sleeve with a spring acting between said handle and said outer sleeve, said handle including a first inner portion for engaging said locking element when at a first position along said axis to maintain said locking element in engagement with said inner and outer sleeves and having a second inner portion for allowing movement of said locking element for releasing said engagement between said inner and outer sleeves when at a second position along said axis.

22. The screw retaining device comprising:
- an inner sleeve extending along a longitudinal axis and having a first end with a gripping segment for selectively gripping and releasing a head of a screw;
- an outer sleeve extending along said axis for sliding engagement with an outer surface of said inner sleeve, said outer sleeve moveable along said axis towards and away from said first end of said inner sleeve and selectively engaging and disengaging said gripping segment causing said selective gripping and releasing of the screw head;

a first locking element mounted on said outer sleeve for selective engagement with said inner sleeve to selectively prevent relative movement therebetween along said axis; and a handle slidably mounted on said outer sleeve with a spring acting between said handle and said outer sleeve, said handle including a first inner portion for engaging said locking element when at a first position along said axis to maintain said locking element in engagement with said inner and outer sleeves and having a second inner portion for allowing movement of said locking element for releasing said engagement between said inner and outer sleeves when at a second position along said axis, wherein movement of said handle along said axis in a direction away from said first end of said inner sleeve causes movement of said handle from said first position to said second position releasing said locking element and causing said outer sleeve to move relative to said inner sleeve under the action of said first spring in a direction away from said first end to selectively release said gripping said screw by said inner sleeve.

23. The screw retaining device comprising:

an inner sleeve extending along a longitudinal axis and having a first end with a gripping segment for:

selectively gripping and releasing a head of a screw;

an outer sleeve extending along said axis for sliding engagement with an outer surface of said inner sleeve, said outer sleeve moveable along said axis towards and away from said first end of said inner sleeve and selectively engaging and disengaging said gripping segment causing said selective gripping and releasing of the screw head;

a first locking element mounted on said outer sleeve for selective engagement with said inner sleeve to selectively prevent relative movement therebetween along said axis: and a handle slidably mounted on said outer sleeve including a first inner portion for engaging said locking element when at a first position along said axis to maintain said locking element in engagement with said inner and outer sleeves and having a second inner portion for allowing movement of said locking element for releasing said engagement between said inner and outer sleeves when at a second position along said axis, wherein said handle portion has an inner bore and said outer sleeve has an outwardly extending collar slidably received within said inner bore of said handle portion, said first locking element mounted in said collar and engaging said inner bore of said handle portion at said first axial position and entering a recess in said handle portion at said second axial position.

* * * * *

UNITED STATES PATENT AND TRADEMARK OFFICE
CERTIFICATE OF CORRECTION

PATENT NO.    : 6,415,693 B1
DATED         : July 9, 2002
INVENTOR(S)   : Simon Bernd and Ole Prien It is certified that error appears in the above-identified patent and that said Letters Patent is hereby corrected as shown below:

Column 2,
Line 57, cancel ",".

Column 3,
Line 23, "56" should read -- 39 --.

Column 4,
Line 46, "bill" should read -- ball --.

Column 7,
Line 24, after "gripping" insert -- of --.

Signed and Sealed this

Fourth Day of February, 2003

JAMES E. ROGAN
*Director of the United States Patent and Trademark Office*